United States Patent [19]
Krul

[11] Patent Number: 4,714,679
[45] Date of Patent: Dec. 22, 1987

[54] IN VITRO PROPAGATION OF GRAPE

[75] Inventor: William R. Krul, Narragansett, R.I.

[73] Assignee: The Board of Governors for Higher Education, State of Rhode Island and Providence Plantations, Providence, R.I.

[21] Appl. No.: 749,306

[22] Filed: Jun. 27, 1985

Related U.S. Application Data

[63] Continuation of Ser. No. 446,442, Dec. 3, 1982.

[51] Int. Cl.⁴ .............................................. A01G 1/00
[52] U.S. Cl. .................................. 435/240.48; 47/58; 435/240.51; 435/240.54
[58] Field of Search ............................. 47/58; 435/240

[56] References Cited

U.S. PATENT DOCUMENTS 4,532,733  8/1985  Krul ........................................ 47/58

Primary Examiner—Robert E. Bagwill
Attorney, Agent, or Firm—Samuels, Gauthier, Stevens & Kehoe

[57] ABSTRACT

A process for controlling the development of somatic embryos for either a self-replicative or a vine development mode. Somatic embryogenesis is initiated by placing the embryo in a medium conducive for self-replication. When the embryos have grown to a first stage, they are transferred to a medium with cytokinin activity. They continue to grow until they have grown to a second stage at which time they are transferred to a medium without cytokinin activity until they have grown sufficiently and can be transferred to a non-liquid growth medium.

1 Claim, 1 Drawing Figure

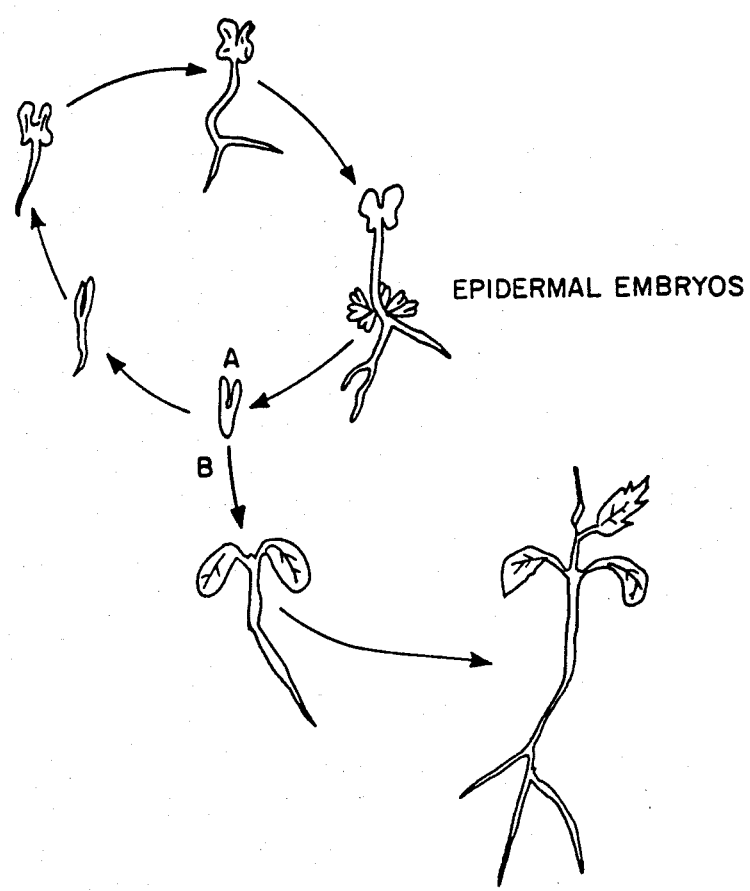

IN VITRO PROPAGATION OF GRAPE

This is a continuation of co-pending application Ser. No. 446,442, filed on Dec. 3, 1982.

The present invention embodies a method of clonal propagation of certain angiosperms and particularly, the hybrid cultivar "Seyval" of the genus Vitis (grapes).

BACKGROUND AND BRIEF SUMMARY OF THE INVENTION

Prior art concerning the propagation of the Vitis species by tissue culture methods is not that prevalent. Currently, there is one report which deals with vine production from fragmented shoot apices; M. Barlass and K. G. M. Skeen (1978), "In vitro propagation of grapevine (Vitis vinifera L.) from fragmented shoot apices." Vitis 17: 335–340. There are two reports which demonstrate the feasibility of producing vines via somatic embryogenesis, Krul and Worley, "Formation of Adventitious Embryo in Callus Cultures of 'Seyval'", J. Amer. Soc. Hort. Sci. 102: 360–363; and M. G. Mullins et al (1976), Somatic Embryos and Plantlets from an Ancient Clone of the Grapevine (cv. Cabernet-Sauvignon) by apomixis in vitro. J. Expt. Bot. 27: 1022–1030. It is possible that grape propagation by shoot tip multiplication may require little or no modification of established methods and therefore, is not reported. See T. Murashige (1974), Plant Propagation Through Tissue Cultures, Annu. Rev. Plant Physiol. 25: 135–166.

In plant propagation, by somatic embryogenesis, i.e. the production of embryonic structures (identical to those in seeds) from isolated plant cells was described in the late 1950's by F. C. Steward et al (1958), Growth and Organized Development of Cultured Cells; II. Organization in cultures grown from freely suspended cells. Amer. J. Bot. 45: 705–708; and J. Reinert, Über die Kontrolle der orphogenese und die Induktion von Adventivembryonen an Gewebekulturen aus Karotten, Planta 53: 318–333.

Embryoids of grape such as other plants arise from proembryonic masses embedded in callus cells. The factors involved in the initiation of proembryonic masses are not known. The transformation of the proembryonic masses to embryoids in grape occurs when they are shifted from a medium containing a active auxin to one containing a less active one; or when the cytokinin level of the medium is lowered. A highly embryogenic callus of 'Seyval' has been isolated which does not require growth regulators for growth. Embryoid formation in this callus occurs when it is grown on auxin for a short while and then cultured on auxin-free media, when the calcium concentration is one half that of the Murashige-Skoog formulation, or when the cultures are grown for long intervals without subculture. Most of the vines regenerated from the original 'Seyval' callus have appeared to be normal. However, a subpopulation of these embryos did not develop normally but produced secondary somatic grape embryos at the junction of the root and shoot.

The development of normal vines from these etiolated secondary grape embryoids is complicated by separate dormancies of the roots, hypocotol, cotyledons and shoot apices, each of which respond to different physical and chemical stimuli.

The processes of successful embryoid production and normal vine development have appeared to be mutually antagonistic. For instance, embryoids which produce embryoids generally senesce and die shortly after embryoid formation. In contrast, embryoids which develop flattened green separate cotyledons or normal shoots generally lose their capacity for the production of secondary embryoids. Therefore, treatments which encourage embryoid production do not favor normal vine development, and conversely, treatments which favor normal vine development restrict somatic embryogenesis.

The production of vines or other plants from isolated cells via somatic embryogenesis is essential for progress in anticipated genetic modifications for plant improvement. Such strategies may involve manipulation in selections of cells tolerant to physical stress (cold or heat) or chemical stress, (herbicidal, bacterial and fungal toxins) or the uptake of gene vectors by protoplasts from embryogenic cells. The use of somatic embryogenesis as an alternative method for the massive production of plants in particular vines has possibilities, but heretofore methods for most cultivars have yet to be developed.

The basic procedures for the mass clonal propagation of certain plants via epidermal cells of somatic embryos is set forth in a publication "In Vitro Propagation of Grape", W. R. Krul and Myerson (1980); Journal Article Number 1932 Rhode Island Agricultural Experimental Station. Also, a detailed discussion of this field is found in a thesis entitled "Adventitious Embryo-genesis and Plantlet Development in Cultures of Vitis vinifera L. 'Seyval'", Judith Myerson thesis submitted to the University of Rhode Island presently on file at the Library of the University of Rhode Island, Kingston, R.I.

I have discovered a method and the plants produced thereby in which somatic embryos may assume either a self-replicating mode or a vine development mode. Prior to my present invention, when a process was employed which was successful in producing self-replicating embryos, the development of normal plants from such embryos occurred at a frequency of about 5%. The present invention permits development of functional plants from such embryos at a frequency in excess of 90%. With the present invention, it is possible to maintain a number of plants in the replicative mode and induce functional plants at times convenient for a producton schedule. The invention is exemplified through the clonal propagation of grape via epidermal cells of somatic embryos of the Vitis cultivar specifically the hybrid 'Seyval'.

Broadly, the cloning process includes removing somatic embryos from a 'mother' plant (see the Drawing, cycle A). Such embryos are cultured for a first time period on a medium, (M/S medium without growth regulators). In this medium, the embryos self-replicate. Subsequently, those embryos which are selected for vine development (see the Drawing, cycle B) are transferred to the same medium with a growth regulator having cytokinin activity and maintained for a fixed period of time in the medium until the desired level of embryo development is reached. At this stage, the embryos are transferred to the same medium without the growth regulator and allowed to develop to allow transplant to soil.

BRIEF DESCRIPTION OF THE DRAWING

The drawing is a schematic of the life cycle of a secondary somatic embryo.

DESCRIPTION OF THE PREFERRED EMBODIMENT

The preferred embodiment of the invention will be described in reference to embryo development in self-replicative and vine development modes.

The maintenance of mother plants and removal of embryos from a mother plant is described in the above-referenced thesis, "Adventitious Embryogenesis and Plantlet Development in Cultures of *Vitis vinifera* L.", 'Seyval', which thesis is hereby incorporated by reference in its entirety in this disclosure.

Adventitious embryogenesis, that is, the initiation of embryos directly from the somatic cells of another embryo or plantlet in culture is not unusual. In the specific non-limiting example set forth below, adventitious embryos, formed on the surface of the root/shoot transition zone of developing 'Seyval' plantlets regenerated from callus, were cultured. These embryos initiated other embryos that also produced embryos, i.e. cloning. Typically, a mother plant will contain anywhere from 0 to 100 such embryos. As is known, it is not usually necessary to physically detach adventitious embryos from the transition zone of the parent plant since most embryos germinate and separate from the parent plant spontaneously.

The life cycle of a secondary somatic embryo of the Vitis species 'Seyval' is illustrated in the FIGURE. Cycle A, the self replicating mode, illustrates the progress of a torpedo stage embryo, through its expansion stage and finally its "reproductive" stage. The cycle requires 30-40 days for completion. Such embryos, when grown on Murashige and Skoog (1962) mineral salts and vitamins supplemented with sucrose and with no plant growth regulators, will remain in the "reproductive" mode, indefinitely. To obtain normal vine development, (pathway B) the torpedo stage embryo, is transferred to M+S media (as above), supplemented with 2.5 uM benzyladenine (BA) for a period of 7 days. When cotyledons become green and begin to separate, the embryo is removed from this medium and placed on the same medium (M+S without BA) until ready for transplanting to a soil mix (approximately 30 days).

Although specific example will be described with reference to 'Seyval' wherein adventitious embryogenesis occurs spontaneously from the root transition zone of plant embryos, without an intervening callus phase, the invention also contemplates embryogenesis or plant development by the following methods of embryo initiation, for example, other types of somatic embryogenesis within the scope of the invention are from callus, from anther or pollen cultures, tumor cells or those transformed by the addition of foreign genes.

Somatic embryos of *Vitis sp.* 'Seyval' produce secondary somatic embryos from epidermal cells at the transition zone between the root and shoot. This process of embryo multiplication (pathway A) occurs when embryos are cultured on MS media plus organics and 3% sucrose (hormone-free media). By transferring embryos produced on mother embryos to hormone-free media, secondary somatic embryogenesis proceeds indefinitely. Most (95%) of the embryos produced do not develop into normal vines; but instead, are arrested at a developmental stage which favors the production of secondary embryos rather than normal shoot development (pathway A, FIG. 1). In the embryo multiplication phase, the embryos have characteristically white unexpanded wrinkled cotyledons (instead of smooth and green) and a dormant shoot apex. About 5% of these embryos develop into normal vines through a process which first involves greening of the cotyledons, and next the growth of the shoot apex (pathway B). It would be desirable to have a means to enhance normal vine development so plants could be multiplied utilizing the embryo multiplication pathway (A) and normal vines obtained by subjecting the somatic embryos to a specific treatment.

The results of the following experiment (EXAMPLE) teaches a process which will enhance normal vine development from somatic embryos (pathway B). The experiment investigated the effects of benzyl adenine on the development of somatic embryos into normal vines (pathway B). Somatic embryo of three different size classes were used to determine if embryo size affects susceptibility to benzyl adenine treatment. Small embryos were of late torpedo stage are characterized by their size (2 mm), their color (white), and the absence of an expanding root or shoot apex. Medium size embryos (2-6 mm) are characterized by their small primary root, small green stem, and white, fused, wrinkled cotyledons. Large embryos are morphologically similar to medium-size embryos but are larger (6-10 mm).

Somatic embryos (cycle A) from the root-hypocotyl transition zone of mother embryos were transferred to either MS media plus vitamins, 3% sucrose, and 2.5 $\mu$M benzyl adenine (BA media) or MS media plus vitamins and 3% sucrose (hormone-free media). After one week of growth on BA media or hormone-free media, embryos were transferred to hormone-free media. During this week, cotyledons of embryos grown on BA greened and shoot development began. However, the cotyledons of untreated embryos remained white and the shoot apex dormant (Table I). BA treatment was most effective on small embryos (Table 1). Once BA treated embryos were transferred to hormone-free media, normal shoot development proceeded and normal vines were obtained without further BA treatment. If larger embryos were used for the BA treatment, fewer normal vines were obtained (Tables 1, 2, and 3). If embryos were grown on BA media for longer than one week, the cotyledons grew abnormally large and leafy and normal vines were not obtained (data not shown). Embryos not treated with BA undergo secondary somatic embryogenesis and produce as many as 70 embryos per mother embryo after 38 days. Embryos treated with BA for one week also produce secondary embryos but generally not to the same extent as untreated embryos.

EXAMPLE

Embryos were removed from mother plants and cultured in hormone-free media (cycle A) and removed when they reach the reproductive stage after 30 to 40 days. The removed embryos were classified according to small, medium and large; small (late torpedo stage) consisting of embryos less than 2 mm; medium (beginning to germinate—root and shoot) consisting of embryos 2-6 mm; and large (older embryos with root and white divided cotyledon) consisting of embryos of 6-10 mm. Sixty embryos, 20 small, 20 medium and 20 large, were maintained for seven (7) days; 10 small, 10 medium and 10 large embryos were maintained in hormone-free media; and 10 small, 10 medium and 10 large embryos were maintained in BA media in 25×150 mm tubes (sealed with kaputs). The BA media comprised 10 ml of Murashige and Skoog media, including vitamin supplements, with 3% sucrose, 0.8% agar, 2.5M BA and pH adjusted to 6 with KOH stock culture (same as culture of mother plant). The hormone-free media was identical less the BA. The final media pH after autoclaving was 5.7. The tubes were placed on 45° slant racks under fluoroscent lights ($10 \times 25$ $uE^{m-2s-1}$), 16 hours photoperiod followed by eight hours darkness a ambient temperatures of between 21°-27° C.

During the seven (7) days, the embryos began to germinate, that is, develop minute shoots, roots, etc. Table I below sets forth the characteristics of the embryos after one week culture in hormone-free media and BA media.

Subsequently, the 10 small, 10 medium and 10 large embryos maintained in the hormone-free media were allowed to continue to culture in hormone-free media for an additional seven (7) days, while the 10 small, 10 medium and 10 large embryos maintained in the BA media were transferred to a hormone-free media as described above. Table II sets forth the plant development of those embryos maintained in the medium with cytokinin activity compared with those embryos maintained in medium without cytokinin activity.

TABLE III-continued

The effect of BA treatment on normal plant development after one week of treatment and four weeks growth on hormone free media.

| Treatment Media | Embryo Size (mm) Before Treatment | % Normal Plants (after one week treatment and three weeks growth on hormone free media) |
|---|---|---|
| BA | Medium (2-6 mm) | 40 |
| HF | Medium | 0 |
| BA | Large (6-10 mm) | 20 |
| HF | Large | 0 |

The embryos maintained in the media containing the cytokinin were allowed to continue to culture in cytokinin-free media as described above. They ultimately developed into normal plants. This is set forth in Table III.

Other cytokinins, both natural and synthetic, may be used to permit the transition from the embryo replicative mode to vine development mode. That is, with the present invention, if it is desired to keep the plant in the self-replicative mode, it is not transferred to the medium with the cytokinin activity, but rather is allowed to

TABLE I

The effect of BA on development of semi-dormant secondary embryos after one week of treatment.
Incubator: 28° C. 16 hr light; 8 hr dark

| Treatment Media | Size of Initial Embryo | 1 PD | 2 | 3 | 4 | 5 #2° embryos | 6 | 7 | 8 | 9 | 10 | % | % |
|---|---|---|---|---|---|---|---|---|---|---|---|---|---|
| BA | Small | GC-0 | GC-0 | GC-0 | GC-0 | GC-0 | GC-0 | GC-0 | GC-0 | GC-0 | GC-0 | 90 GC | 10WC |
| HF | Small | WC-0 | WC-0 | WC-0 | WC-0 | WC-0 | WC-0 | WC-0 | WC-0 | WC-0 | WC-0 | | 100WC |
| BA | Medium | GC-0 | WC-0 | WC-0 | WC-0 | WC-0 | GC-0 | WC-0 | WC-0 | GC-0 | GC-0 | 40GC | 60WC |
| HF | Medium | WC-0 | WC-0 | WC-0 | WC-0 | WC-0 | WC-0 | WC-2 | WC-0 | WC-0 | WC-0 | | 100WC |
| BA | Large | WC-0 | GC-0 | WC-0 | WC-0 | GC-0 | WC-0 | WC-0 | WC-0 | WC-0 | WC-0 | 20GC | 80WC |
| HF | Large | WC-0 | WC-0 | WC-0 | WC-0 | WC-0 | WC-0 | WC-1 | WC-2 | WC-0 | WC-0 | | 100WC |

Treatment Media
BA = Benzyl Adenine
HF = Hormone Free

Plant Development (PD)
GC = Green Cotyledon
WC = White Cotyledon

TABLE II

The effect of BA treatment on development of semi-dormant somatic embryos after one week of treatment and one week of growth hormone free media.

| Treatment Media | Embryo Size Prior to Treatment | 1 PD | 2 | 3 | 4 | 5 #2° Embryos | 6 | 7 | 8 | 9 | 10 | NUMBER | | | |
|---|---|---|---|---|---|---|---|---|---|---|---|---|---|---|---|
| BA | Small | GCA-0 | GC-0 | GC-1 | GC-0 | WC-0 | GCA-0 | GCA-0 | P-0 | GC-1 | GC-0 | 1P | 3GCA | 5GC | 1WC |
| HF | Small | WC-0 | WC-0 | WC-0 | WC-0 | WC-0 | WC-0 | WC-0 | WC-0 | WC-2 | WC-0 | | | | 10WC |
| BA | Medium | GCA-5 | WCA-6 | WC-0 | WC-0 | WC-5 | GC-1 | WC-0 | WC-0 | GC-0 | GC-0 | 1WCA | 1GCA | 3GC | 5WC |
| HF | Medium | WC-0 | WC-0 | WC-0 | WC-0 | WC-0 | WC-3 | WC-1 | WC-2 | WC-1 | WC-2 | | | | 10WC |
| BA | Large | WC-0 | GC-0 | WC-2 | WC-0 | GC-0 | WC-0 | WC-0 | WC-1 | WC-3 | WC-0 | | | | |
| HF | Large | WC-0 | WC-0 | WC-0 | WC-1 | WC-0 | WC-3 | WC-1 | WC-2 | WC-0 | WC-0 | 2GC | 8WC | | 10WC |

Treatment Media
BA = Benzyl Adenine
HF = Hormone Free

Plant Development (PD)
WC = White Cotyledon
GC = Green Cotyledon
A = Apex between GC or WC
P = Plant

TABLE III

The effect of BA treatment on normal plant development after one week of treatment and four weeks growth on hormone free media.

| Treatment Media | Embryo Size (mm) Before Treatment | % Normal Plants (after one week treatment and three weeks growth on hormone free media) |
|---|---|---|
| BA | Small (<2 mm) | 90 |
| HF | Small | 0 | continue to develop, which development will result in poor to nonexistent plant development, but very satisfactory embryo multiplication. Where it is desired to have the embryos enter the vine development mode, then they are transferred to the medium with the cytokinin activity as just described.

The invention has been described with reference to the cytokinin activity of 2.5 uM benzyl adenine. Within the scope of the invention, other natural and synthetic cytokinins which will permit transition from the embryo replicative mode to the normal vine growth and development mode include zeatin and its riboside and ribotide; isopentenyl adenine and its riboside and ribotide; kinetin; ethyoxyethyladenine; 2-2 hydroxyzeatin; N,N$^1$-diphenylurea and 8-azakinetin. Although described in reference to a concentration of cytokinin activity of 2.5 uM, within the scope of the invention various concentrations of cytokinin which will promote the desired activity are contemplated. The cytokinins may be used alone or in combination.

It is believed that two factors play an important part in the development of normal plants from these embryos, namely the size of the embryo when transferred to the medium with cytokinin activity and the length of time that the plant is allowed to remain in the medium with the cytokinin activity. More specifically, control of the growth of the embryos in any suitable medium until such time as the embryos evidence signs of germinating, i.e. development of roots, shoots, etc., is the first step. When the embryo should physically be removed for transfer to media with cytokinin activity, the embryo may be generally characterized by the following: (a) less than 2 mm long, consisting of visible cotyledon, hypocotyl and root. The color of the embryo is mostly an opaque ivory white with the root zone characterized by yellowish translucent tissue. The cotyledons are appressed and have not yet completed expansion and final shape is not yet assumed. Approximately ⅓ of the embryo mass consist of cotyledonary tissue. The root zone appears to be in the primorida stage, e.g. still in the cell division stage, as no cell elongation is obvious. The root mass is approximately ¼ (or less) of the total embryo. The correct morphological descriptor for embryo at this stage of development is late torpedo stage.

After embryo development has reached the stage as described above, if it is desired that the embryos should continue to development to self-replicative (i.e. produce more embryos), then they are simply allowed to remain in the same or a similar medium. If it is desired that the embryos be transferred to the vine development mode, then they are transferred to a medium with cytokinin activity. The duration of time during which the embryos remain in the medium with the cytokinin activity for a fixed period of time is critical. This fixed period of time is sufficient to insure that the embryos as germinating do not become either underdeveloped or overdeveloped, in which cases normal vine development will not occur. The development stage at which the embryos must be removed may be described as follows: cotyledons divided and green—apex may or may not be visible.

Although described in reference to the hybrid 'Seyval', other plants classified as follows are within the scope of my invention: All genera with the potential to form somatic embryo from isolated cells.

Having described my invention, what I now claim is:

1. A method for controlling the growth of plant embryos for either self-replicative or vine development modes, which includes:
   (a) initiating somatic embryogenesis by placing callus cultures in a medium conducive for self-replication of embryos for a first period of time during which the embryos germinate and are characterized by late torpedo stage embryos prior to root and shoot elongation;
   (b) culturing for vine development at least some of the embryos of step (a) in a medium having cytokinin activity for a second period of time at the end of which time the embryos are characterized by green divided cotyledons;
   (c) transferring the embryos of step (b) to a medium free of cytokinin activity until such time that they develop sufficiently for transfer to a non-agar growth support medium.

* * * * *